United States Patent
Collins et al.

(10) Patent No.: US 8,309,336 B2
(45) Date of Patent: Nov. 13, 2012

(54) FAMILY 8 ENZYMES WITH XYLANOLYTIC ACTIVITY

(75) Inventors: Tony Collins, Coolanuller (IE); Georges Feller, Trooz (BE); Charles Gerday, Esneux (BE); Marie-Alice Meuwis, Liege (BE)

(73) Assignee: Université de Liège, Liège (BE)

( * ) Notice: Subject to any disclaimer, the term of this patent is extended or adjusted under 35 U.S.C. 154(b) by 0 days.

(21) Appl. No.: 12/868,523

(22) Filed: Aug. 25, 2010

(65) Prior Publication Data

US 2011/0039325 A1 Feb. 17, 2011

Related U.S. Application Data

(62) Division of application No. 10/527,387, filed as application No. PCT/BE03/00152 on Sep. 11, 2003, now Pat. No. 8,192,772.

(60) Provisional application No. 60/410,345, filed on Sep. 11, 2002.

(51) Int. Cl.
*C12N 9/00* (2006.01)
*C12N 9/24* (2006.01)
*C12N 1/20* (2006.01)
*C12N 15/00* (2006.01)
*C07H 21/04* (2006.01)

(52) U.S. Cl. ............ 435/200; 435/183; 435/252.3; 435/320.1; 536/23.2

(58) Field of Classification Search .................. None
See application file for complete search history.

(56) References Cited

U.S. PATENT DOCUMENTS

| | | | |
|---|---|---|---|
| 6,110,508 | A | 8/2000 | Olesen et al. |
| 6,346,407 | B1 | 2/2002 | De Buyl et al. |
| 2003/0059497 | A1 | 3/2003 | Teran |
| 2003/0082779 | A1 | 5/2003 | Dunn-Coleman et al. |

FOREIGN PATENT DOCUMENTS

| | | |
|---|---|---|
| WO | WO 95/23515 A | 9/1995 |
| WO | WO 96/32472 A | 10/1996 |
| WO | WO 01/70998 A1 | 9/2001 |
| WO | WO 02/19828 A1 | 3/2002 |
| WO | WO 2004/023879 A | 3/2004 |

OTHER PUBLICATIONS

Collins et al. J Biol Chem. Sep. 20, 2002;277(38):35133-9. Epub Jun. 27, 2002.*
Accession Q8RJN8, Jun. 1, 2002.*
Collins, T. et al. (2002) "A Novel Family 8 Xylanase: Functional and Physicochemical Characterization" *J. Biol. Chem.* 277:35133-35139.
Van Petegem, F. et al. (2003) "The Structure of a Cold-adapted Family 8 Xylanase at 1.3 Å Resolution. Structural Adaptations to Cold and Investigation of the Active Site." *J. Biol. Chem.* vol. 278, No. 9, pp. 7531-7539.
Gil, M.J. et al. "Keeping qualities of white pan bread upon storage: effect of selected enzymes on bread firmness and elasticity." Z Lebensm Unters Forsch A. 208: pp. 394-399 (1999).
Machine Translation of JP 2001-245665-A (2001).
Gerday, C., et al. "Cold adapted enzymes: from fundamentals to biotechnology." Trends in Biotechnology, 18:103-107 (2000).
McCleary, B. V., "Enzymatic Modification of Plant Polysaccharides," Int. J. Biol. Macromol., 1986, pp. 349-354, vol. 8.
Plesniak, L. A., et al., "Secondary Structure and NMR Assignments of *Bacillus circulans* Xylanase," Protein Science, 1996, pp. 1118-1135, vol. 5.
Rouau, X., et al., "Effect of an Enzyme Preparation Containing Pentosanases on the Bread-making Quality of Flours in Relation to Changes in Pentosan Properties," Journal of Cereal Science, 1994, pp. 259-272, vol. 19.

* cited by examiner

*Primary Examiner* — Christian Fronda
(74) *Attorney, Agent, or Firm* — Senniger Powers LLP

(57) ABSTRACT

The present invention describes a method to improve the properties of a dough and/or a baked product by adding a bread or dough-improving agent containing a enzyme with xylanolytic activity belonging to glycoside hydrolases family 8. Preferred enzymes are the psychrophilic xylanase from *Pseudoalteromonas haloplanktis* and the mesophilic xylanase Y from *Bacillus halodurans* C-125.

6 Claims, 1 Drawing Sheet

SEQUENCE LISTING

<160> NUMBER OF SEQ ID NOS: 8

<210> SEQ ID NO 1
<211> LENGTH: 28
<212> TYPE: DNA
<213> ORGANISM: Artificial Sequence
<220> FEATURE:
<223> OTHER INFORMATION: sense primer

<400> SEQUENCE: 1
gggcatatga agaaaacgac agaaggtg                28

<210> SEQ ID NO 2
<211> LENGTH: 26
<212> TYPE: DNA
<213> ORGANISM: Artificial Sequence
<220> FEATURE:
<223> OTHER INFORMATION: antisense primer

<400> SEQUENCE: 2
ggctcgagct agtgttcctc ttcttg                26

<210> SEQ ID NO 3
<211> LENGTH: 20
<212> TYPE: DNA

```
<213> ORGANISM: Artificial Sequence
<220> FEATURE:
<223> OTHER INFORMATION: sequencing primer

<400> SEQUENCE: 3
gtgcggactg aaggaatgtc                                              20

<210> SEQ ID NO 4
<211> LENGTH: 20
<212> TYPE: DNA
<213> ORGANISM: Artificial Sequence
<220> FEATURE:
<223> OTHER INFORMATION: sequencing primer

<400> SEQUENCE: 4
gtatggtcca tcaacagagg                                              20

<210> SEQ ID NO 5
<211> LENGTH: 21
<212> TYPE: DNA
<213> ORGANISM: Artificial Sequence
<220> FEATURE:
<223> OTHER INFORMATION: sequencing primer

<400> SEQUENCE: 5
gatggcacta aaaactcctg g                                            21

<210> SEQ ID NO 6
<211> LENGTH: 1281
<212> TYPE: DNA
<213> ORGANISM: Pseudoalteromonas haloplanktis
<220> FEATURE:
<221> NAME/KEY: misc_feature
<222> LOCATION: (0)...(0)
<223> OTHER INFORMATION: xylanase gene of Pseudoalteromonas haloplanktis
      (EMBL accession number AJ427921)

<400> SEQUENCE: 6
atgaaagtat tttttaaaat aacaacttta ttgttaatac taataagcta tcaatcactt    60
gctgcattta taataacccc atcgagtgta ggcgcctaca gttcagggac ataccgtaac   120
ctcgcacaag aaatgggtaa acaaatata cagcaaaagg tgaatagtac ttttgacaat   180
atgtttggct ataacaacac acaacaactt tactacccgt acaccgaaaa cggtgtttat   240
aaagcacact acataaaagc aattaaccca gacgaaggcg acgatataag aacagaaggg   300
caatcgtggg gaatgaccgc cgctgtcatg cttaataaac aagaagaatt tgataaccta   360
tggcgctttg caaaagcgta tcaaaaaaat ccagacaatc ccctgatgc taaaaaacaa   420 ggcgtttacg cgtggaaact aaagcttaat caaaacggct tgtttataa agtggatgag   480 ggccccgctc ccgatggcga agagtacttt gcgtttgcac tacttaatgc ctctgctcgt   540
tgggggaatt cgggtgagtt taactactac aacgatgcca ttaccatgtt aaacacaatt   600
aaaaataagc tgatggaaaa ccaaataatc cgcttttcac cttacattga taacctaaca   660
gacccttctt accatatacc tgcgttttac gactactttg caaataacgt aactaaccaa   720
gcagacaaaa attactggcg acaagtagcc acaaaaagta gaaccttact taaaaaccat   780
tttacaaaag taagtggtag cccgcattgg aacttaccta cattttatc gcgcttagat   840 ggcagccctg ttattggcta cattttaac ggccaagcaa acccaggtca atggtatgaa   900
tttgatgcat ggcgcgtaat tatgaatgtg ggtttagacg cgcatttaat gggtgctcaa   960
gcgtggcata aaagtgcagt taataaagca ctgggctttt taagttatgc aaaaacaaac  1020
aacagtaaaa actgttacga gcaagtgtat tcgtacggtg gagcgcaaaa cagaggctgt  1080
```

-continued

```
gcaggcgaag gtcaaaaagc cgcgaatgca gtagcgttac ttgcttcaac aaatgctggg    1140
caagcaaatg agttttttaa cgaatttggg tctttatcgc aaccaacggg tgactaccgt    1200
tactataatg gttcgttata tatgttagct atgctgcatg tatcgggcaa ttttaagttt    1260
tataacaaca cgtttaatta a                                              1281
```

<210> SEQ ID NO 7
<211> LENGTH: 426
<212> TYPE: PRT
<213> ORGANISM: Pseudoalteromonas haloplanktis
<220> FEATURE:
<221> NAME/KEY: VARIANT
<222> LOCATION: (0)...(0)
<223> OTHER INFORMATION: xylanase of Pseudoalteromonas haloplanktis
    (EMBL accession number AJ427921)

<400> SEQUENCE: 7

```
Met Lys Val Phe Phe Lys Ile Thr Thr Leu Leu Leu Ile Leu Ile Ser
  1               5                  10                  15

Tyr Gln Ser Leu Ala Ala Phe Asn Asn Asn Pro Ser Ser Val Gly Ala
             20                  25                  30

Tyr Ser Ser Gly Thr Tyr Arg Asn Leu Ala Gln Glu Met Gly Lys Thr
         35                  40                  45

Asn Ile Gln Gln Lys Val Asn Ser Thr Phe Asp Asn Met Phe Gly Tyr
     50                  55                  60

Asn Asn Thr Gln Gln Leu Tyr Tyr Pro Tyr Thr Glu Asn Gly Val Tyr
 65                  70                  75                  80

Lys Ala His Tyr Ile Lys Ala Ile Asn Pro Asp Glu Gly Asp Asp Ile
                 85                  90                  95

Arg Thr Glu Gly Gln Ser Trp Gly Met Thr Ala Ala Val Met Leu Asn
            100                 105                 110

Lys Gln Glu Glu Phe Asp Asn Leu Trp Arg Phe Ala Lys Ala Tyr Gln
        115                 120                 125

Lys Asn Pro Asp Asn His Pro Asp Ala Lys Lys Gln Gly Val Tyr Ala
    130                 135                 140

Trp Lys Leu Lys Leu Asn Gln Asn Gly Phe Val Tyr Lys Val Asp Glu
145                 150                 155                 160

Gly Pro Ala Pro Asp Gly Glu Glu Tyr Phe Ala Phe Ala Leu Leu Asn
                165                 170                 175

Ala Ser Ala Arg Trp Gly Asn Ser Gly Glu Phe Asn Tyr Tyr Asn Asp
            180                 185                 190

Ala Ile Thr Met Leu Asn Thr Ile Lys Asn Lys Leu Met Glu Asn Gln
        195                 200                 205

Ile Ile Arg Phe Ser Pro Tyr Ile Asp Asn Leu Thr Asp Pro Ser Tyr
    210                 215                 220

His Ile Pro Ala Phe Tyr Asp Tyr Phe Ala Asn Asn Val Thr Asn Gln
225                 230                 235                 240

Ala Asp Lys Asn Tyr Trp Arg Gln Val Ala Thr Lys Ser Arg Thr Leu
                245                 250                 255

Leu Lys Asn His Phe Thr Lys Val Ser Gly Ser Pro His Trp Asn Leu
            260                 265                 270

Pro Thr Phe Leu Ser Arg Leu Asp Gly Ser Pro Val Ile Gly Tyr Ile
        275                 280                 285

Phe Asn Gly Gln Ala Asn Pro Gly Gln Trp Tyr Glu Phe Asp Ala Trp
    290                 295                 300

Arg Val Ile Met Asn Val Gly Leu Asp Ala His Leu Met Gly Ala Gln
```

-continued

```
                305                 310                 315                 320
Ala Trp His Lys Ser Ala Val Asn Lys Ala Leu Gly Phe Leu Ser Tyr
            325                 330                 335

Ala Lys Thr Asn Asn Ser Lys Asn Cys Tyr Glu Gln Val Tyr Ser Tyr
            340                 345                 350

Gly Gly Ala Gln Asn Arg Gly Cys Ala Gly Glu Gly Gln Lys Ala Ala
            355                 360                 365

Asn Ala Val Ala Leu Leu Ala Ser Thr Asn Ala Gly Gln Ala Asn Glu
            370                 375                 380

Phe Phe Asn Glu Phe Trp Ser Leu Ser Gln Pro Thr Gly Asp Tyr Arg
385                 390                 395                 400

Tyr Tyr Asn Gly Ser Leu Tyr Met Leu Ala Met Leu His Val Ser Gly
                405                 410                 415

Asn Phe Lys Phe Tyr Asn Asn Thr Phe Asn
            420                 425

<210> SEQ ID NO 8
<211> LENGTH: 388
<212> TYPE: PRT
<213> ORGANISM: Bacillus halodurans
<220> FEATURE:
<221> NAME/KEY: VARIANT
<222> LOCATION: (0)...(0)
<223> OTHER INFORMATION: xylanase Y from Bacillus halodurans strain
      C-125 (GenBank/GenPeptTM accession code BAB05824)

<400> SEQUENCE: 8

Met Lys Lys Thr Thr Glu Gly Ala Phe Tyr Thr Arg Glu Tyr Arg Asn
 1               5                  10                  15

Leu Phe Lys Glu Phe Gly Tyr Ser Glu Ala Glu Ile Gln Glu Arg Val
            20                  25                  30

Lys Asp Thr Trp Glu Gln Leu Phe Gly Asp Asn Pro Glu Thr Lys Ile
            35                  40                  45

Tyr Tyr Glu Val Gly Asp Asp Leu Gly Tyr Leu Leu Asp Thr Gly Asn
        50                  55                  60

Leu Asp Val Arg Thr Glu Gly Met Ser Tyr Gly Met Met Met Ala Val
65                  70                  75                  80

Gln Met Asp Arg Lys Asp Ile Phe Asp Arg Ile Trp Asn Trp Thr Met
                85                  90                  95

Lys Asn Met Tyr Met Thr Glu Gly Val His Ala Gly Tyr Phe Ala Trp
            100                 105                 110

Ser Cys Gln Pro Asp Gly Thr Lys Asn Ser Trp Gly Pro Ala Pro Asp
            115                 120                 125

Gly Glu Glu Tyr Phe Ala Leu Ala Leu Phe Phe Ala Ser His Arg Trp
            130                 135                 140

Gly Asp Gly Asp Glu Gln Pro Phe Asn Tyr Ser Glu Gln Ala Arg Lys
145                 150                 155                 160

Leu Leu His Thr Cys Val His Asn Gly Glu Gly Pro Gly His Pro
            165                 170                 175

Met Trp Asn Arg Asp Asn Lys Leu Ile Lys Phe Ile Pro Glu Val Glu
            180                 185                 190

Phe Ser Asp Pro Ser Tyr His Leu Pro His Phe Tyr Glu Leu Phe Ser
            195                 200                 205

Leu Trp Ala Asn Glu Glu Asp Arg Val Phe Trp Lys Glu Ala Ala Glu
            210                 215                 220

Ala Ser Arg Glu Tyr Leu Lys Ile Ala Cys His Pro Glu Thr Gly Leu
225                 230                 235                 240
```

```
Ala Pro Glu Tyr Ala Tyr Tyr Asp Gly Thr Pro Asn Asp Glu Lys Gly
                245                 250                 255

Tyr Gly His Phe Phe Ser Asp Ser Tyr Arg Val Ala Ala Asn Ile Gly
            260                 265                 270

Leu Asp Ala Glu Trp Phe Gly Gly Ser Glu Trp Ser Ala Glu Glu Ile
        275                 280                 285

Asn Lys Ile Gln Ala Phe Phe Ala Asp Lys Glu Pro Glu Asp Tyr Arg
    290                 295                 300

Arg Tyr Lys Ile Asp Gly Glu Pro Phe Glu Glu Lys Ser Leu His Pro
305                 310                 315                 320

Val Gly Leu Ile Ala Thr Asn Ala Met Gly Ser Leu Ala Ser Val Asp
                325                 330                 335

Gly Pro Tyr Ala Lys Ala Asn Val Asp Leu Phe Trp Asn Thr Pro Val
            340                 345                 350

Arg Thr Gly Asn Arg Arg Tyr Tyr Asp Asn Cys Leu Tyr Leu Phe Ala
        355                 360                 365

Met Leu Ala Leu Ser Gly Asn Phe Lys Ile Trp Phe Pro Glu Gly Gln
    370                 375                 380

Glu Glu Glu His
385
```

FAMILY 8 ENZYMES WITH XYLANOLYTIC ACTIVITY

RELATED APPLICATIONS

This application is a divisional of U.S. application Ser. No. 10/527,387, filed Oct. 17, 2005, which is the U.S. National Phase of PCT/BE2003/000152, filed Sep. 11, 2003, designating the United States and published in English on Mar. 25, 2004, as WO2004/023879, which claims the benefit of U.S. Provisional Patent Application No. 60/410,345, filed Sep. 11, 2002. The contents of these applications are incorporated herein by reference in their entireties.

SEQUENCE LISTING

The present application is being filed along with a Sequence Listing in electronic format. The Sequence Listing is provided as a file entitled VANM262_001DV2_final.TXT, created Aug. 25, 2010, which is 9.92 Kb in size. The information in the electronic format of the Sequence Listing is incorporated herein by reference in its entirety.

FIELD OF THE INVENTION

The present invention concerns a method and a composition for the improvement of bakery products that comprise at least one enzyme with xylanolytic activity from the glycoside hydrolases family 8. In an embodiment of the invention said enzyme with xylanolytic activity is further characterized by the fact that there is an inversion of configuration during hydrolysis. In specific embodiments of the invention said enzyme with xylanolytic activity is a psychrophilic xylanase from *Pseudoalteromonas haloplanktis* or a mesophilic xylanase from *Bacilllus halodurans*.

BACKGROUND OF THE INVENTION

Xylans are heteropolysaccharides that form the major part of the hemicellulose present in the plant biomass. The backbone of these polysaccharides is a chain of β 1-4 linked xylopyranosyl residues. Many different side groups could bind to these residues like acetyl, arabinosyl and glucuronosyl residues. Phenolic compounds such as ferulic or hydroxycinnamic acids are also involved through ester binding in the cross linking of the xylan chains or in the linkage between xylan and lignin chains for example.

Endoxylanases (or endo-β-1,4-xylanases) hydrolyse specifically the backbone of the hemicellulose. In some cases, the side groups may mask the main chain by steric hindrance. Different xylanases activities have been described. Their specificity towards their substrate varies from one to each other. Some are more active on insoluble arabinoxylans. The length of the oligomers produced also depends on the type of xylanase considered.

Glycoside hydrolases (formerly known as cellulase family D) have been classified in 91 families (http://afmb.cnrs-mrs.fr/CAZY/) based on sequence homologies, structural and mechanistic features. Because the fold of proteins is better conserved than their sequences, some of the families can be grouped in 'clans' (Henrissat B. 1991, Biochem. J. Vol. 280, p 309). Endo-beta-1,4-xylanases are generally classified in families 10 (formerly family F) and 11 (formerly family G) and are found to frequently have an inverse relationship between their pI and molecular weight. The family 10 xylanases (EXs10) are larger, more complex, while the family 11 xylanases (EXs11) are smaller. Moreover a significant difference in the structure and the catalytic properties of both families exists. EXs10 present an (α/β)8 barrel fold, have about 40% of α-helix structures and belong to clan GH-A (Dominguez et al., 1995, Nat. Struct. Biol. Vol. 2, p 569) while EXs11 exhibit a β-jelly fold conformation, have about 3-5% of α-helix structures and belong to clan GH-C (Törrönen et al., 1994, EMBO J. Vol. 13, p 2498). EXs10 have a smaller substrate binding site and a lower substrate specificity, have frequently endoglucanase activity and produce smaller oligosaccharides compared to EXs11, which have a higher affinity for unsubstituted xylan (Biely et al., 1997, J. Biotechnol. Vol. 57, p 151). All xylanases of both families characterized to date retain the anomeric configuration of the glycosidic oxygen following hydrolysis in which two glutamates function as the catalytic residues (Jeffries, 1997, Curr. Opin. Biotechnol. Vol. 7, p 337).

Xylanases are used in various industrial areas such as the pulp, paper, feed and bakery industries. Other applications lie in the juice and beer sectors. Xylanases could also be used in the wheat separation process. The observed technological effects are, among others, improved bleachability of the pulp, decreased viscosity of the feed or changes in dough characteristics.

The use of xylanases (also called hemicellulases or pentosanases) in baking is well known since a number of years. These dough-conditioning enzymes can improve the dough machinability and stability as well as the oven-spring and the crumb structure. Other effects of the enzymes are a larger loaf volume and a softer crumb.

The mechanism of action of xylanases in bread preparation is still not clearly elucidated. There are about 3 to 4% pentosans in wheat flour. These pentosans can absorb large amounts of water (up to 30%). This water absorption contributes to the properties of the dough as well as to the quality of the final product. Partial hydrolysis of pentosans by pentosanases into water soluble short chain oligosaccharides increases the water binding capacity. There is also a strong interaction of the pentosans with the gluten fraction of the flour to form a network. Pentosanases may help to relax this strong and rigid network and therefore allowing the carbon dioxide formed by the yeast to better expand the dough.

Many types of hemicellulase preparations have been used as baking active-ingredients and are commercially available. They are produced by microbial fermentation using various microorganisms as enzyme sources. Some of these enzymes are also produced by genetically modified microorganisms. All documented uses of xylanases having a positive effect on the specific volume of baked goods, relate to xylanases belonging to glycoside hydrolases Family 10 or Family 11 as defined previously.

Examples of xylanases for baking are the xylanases from *Bacillus subtilis* and *Aspergillus niger*.

There is a variety of methods to evaluate the xylanase activity in an enzyme preparation. Examples of such methods of xylanase activity determination are the measure of the release of reducing sugar from xylan (Miller G. L. 1959, Anal. Chem. Vol. 31, p 426) or the measure of the release of coloured compounds from modified substrates (for examples AzoWAX or Xylazyme AX from Megazyme). However no direct correlation could be found between the xylanolytic activity found in the various enzyme preparations and the effect in baking. Dose-related results can be observed to a certain extend for a single enzyme but the same dosage for two xylanases of different origins does not give the same result in the dough or in the bread. Several reasons could explain this: the differences in substrate specificity, the differences in temperature and pH optimum, . . . .

It is of great interest to develop new enzyme preparations, such as bread improver compositions or agents, with new or improved properties. One of these properties could be that the xylanase fraction is as small as possible (in terms of weight of enzymes needed to obtain a particular result in baking).

A xylanase from the Antarctic bacterium *Pseudoalteromonas haloplanktis* has been recently described (Collins, T. et al. 2002. A novel Family 8 xylanase: functional and physicochemical characterisation. J. Biol. Chem. Vol. 277-38, p 35133; Collins, T. et al. 2003, Activity, stability and flexibility in glycosidases adapted to extreme thermal environments. J. Mol. Biol. Vol. 328, p 419; Van Petegem F. et al., 2002. Crystallization and preliminary X-ray analysis of a xylanase from the psychrophile *Pseudoalteromonas haloplanktis*. Acta Crystallogr D Biol Crystallogr. Vol. 58(Pt 9), p 1494-6). This enzyme is a typical psychrophilic enzyme and presents a high catalytic activity at low temperature. It is not homologous to family 10 or 11 xylanases but has 20 to 30% identity with glycoside hydrolases family 8 (formerly family D) members, a family that comprises mainly endoglucanases but also lichenases and chitosanases. Furthermore, a FingerPRINTScan against PRINTS using the InterPro Scan search program (Zdobnov and Apweiler, 2001, Bioinformatics Vol. 17, p 847) indicated that the isolated sequence contained the glycosyl hydrolases family 8 fingerprint and family 8 residues that are strictly conserved in 20 family 8 enzymes analyzed.

Conversely to EXs10 and EXs11, this family 8 xylanase (EXs8) has both high pH and high molecular weight. Structural and catalytic properties are different to those of both EXs10 and EXs11. EXs8 present an ($\alpha/\alpha$)6 barrel fold with 13 $\alpha$-helices and 13 $\beta$-strands and belong to clan GH-M (Van Petegem et al., 2003, The structure of a cold-adapted family 8 xylanase at 1.3 A resolution. Structural adaptations to cold and investigation of the active site. J. Biol. Chem. Vol. 278(9), p 7531-9). These enzymes have no endoglucanase, chitosanase or licheninase activity and appear to be functionally similar to EXs11, being more active on long chain xylo-oligosaccharides.

In contrast to other known EXs10 and EXs11 that retain the configuration, family 8 glyco-hydrolases (Fierobe et al., 1993. Eur. J. Biochem. Vol. 217, p 557; http://afmb.cnrs-mrs.fr/CAZY/) tend to hydrolyse the substrate with inversion of the anomeric configuration of the glycosidic oxygen following hydrolysis in which one glutamate and one aspartate function as the catalytic residues. This has been shown for example for the psychrophilic xylanase from *Pseudoalteromonas haloplanktis* (Van Petegem et al., 2003, J. Biol. Chem., Vol. 278(9), p 7531-9; Collins, T. et al. 2002. A novel family 8 xylanase: functional and physico-chemical characterization. J. Biol. Chem. Vol. 277(38), p 35133). Other xylanases belonging to the glycoside hydrolases family 8 have been already described (Yoon, K-H., 1998, Molecular cloning of a *Bacillus* sp. KK-1 xylanase gene and characterization of the gene product. Biochem. Mol. Biol. International. 45(2), p. 337; *Bacillus halodurans* C-125 xylanase Y GenBank/GenPept™ accession code BAB05824). These xylanases show sequence homologies between them as well as with the *Pseudoalteromonas haloplanktis* xylanase as described by Collins et al (2002, see above).

The list of the enzymes belonging to the glycoside hydrolases family 8 is regularly updated (http://afmb.cnrs-mrs.fr/CAZY/).

AIMS OF THE INVENTION

The present invention aims to provide novel enzyme preparations such as bread improver compositions.

The present invention further aims to provide a new method for obtaining improved bakery products by using such enzyme preparations.

SUMMARY OF THE INVENTION

It was surprisingly found that an enzyme with xylanolytic activity and belonging to glycoside hydrolases family 8 had a positive effect on the dough properties or on the baked product properties when it was added during the mixing of the dough.

It was also surprisingly found that an enzyme with xylanase activity and hydrolysing with inversion of the anomeric configuration had a positive effect on the dough properties or on the baked products properties when it was added during the mixing of the dough.

It was further surprisingly found that the use of enzymes as described above increases the volume of the loaf.

It was also found that the use of some such enzymes with xylanolytic activity from the glycoside hydrolases family 8, the EXs8, make it possible to use less enzyme for the same effect on the dough or bread properties as compared to presently known xylanases.

A specific embodiment of this invention concerns enzymes with xylanolytic activity from the glycoside hydrolases family 8 and their use in the baking industry as described above.

A particular embodiment of the invention concerns a psychrophilic family 8 xylanase from *Pseudoalteromonas haloplanktis* and a mesophilic family 8 xylanase Y from *Bacillus halodurans*. These enzymes are xylanases that hydrolyze with inversion of the anomeric configuration.

Preferred xylanases are those obtained from the strains *Pseudoalteromonas haloplanktis* TAH3a, and *Bacillus halodurans* C-125 or those obtained from the corresponding gene expressed in a suitable host.

Preferably, the bread improving composition comprising at least one enzyme of the invention is added during the mixing of the dough.

Said bread improving composition may further comprise other bread-improving agents selected from the list consisting of other enzymes, emulsifiers, oxidants, milk powder, fats, sugars, amino acids, salts, proteins (gluten, cellulose binding sites) or a mixture thereof.

Said other enzymes may be selected from the list consisting of alpha-amylases, beta-amylases, maltogenic amylases, other xylanases, proteases, glucose oxidase, oxido-reductases, glucanases, cellulases, transglutaminases, isomerases, lipases, phospholipases, pectinases or a mixture thereof.

Said alpha-amylase preferably is obtained from *Aspergillus oryzae*.

The enzymes with xylanolytic activity according to the invention may be used in the form of a cell extract, a cell-free extract or as a purified protein in said bread improving composition.

The enzymes of the invention may be mixed with other ingredients and be used in the form of a dry powder or a granulate, in particular a non-dusting granulate, or in the form of a liquid, preferably with one or more stabilizer(s) such as polyols, sugars, organic acids or sugar alcohols.

Another aspect of the invention concerns baked products obtained or obtainable when using an enzyme of the invention.

A further aspect of the invention concerns bread improving compositions comprising at least one of the enzymes of the invention.

A still further aspect of the invention concerns a method for increasing the loaf volume of a baked product, comprising the step of adding during the mixing of the dough of said baked product, a sufficient amount of an enzyme with xylanolytic activity selected from the group consisting of glycoside hydrolase family 8 xylanases, possibly enzymes with xylanolytic activity that hydrolyze with inversion of configuration. It is possible to use any combination or mixture of the above described enzymes in a dough or bakery product for any of the above described purposes.

Figure 1:
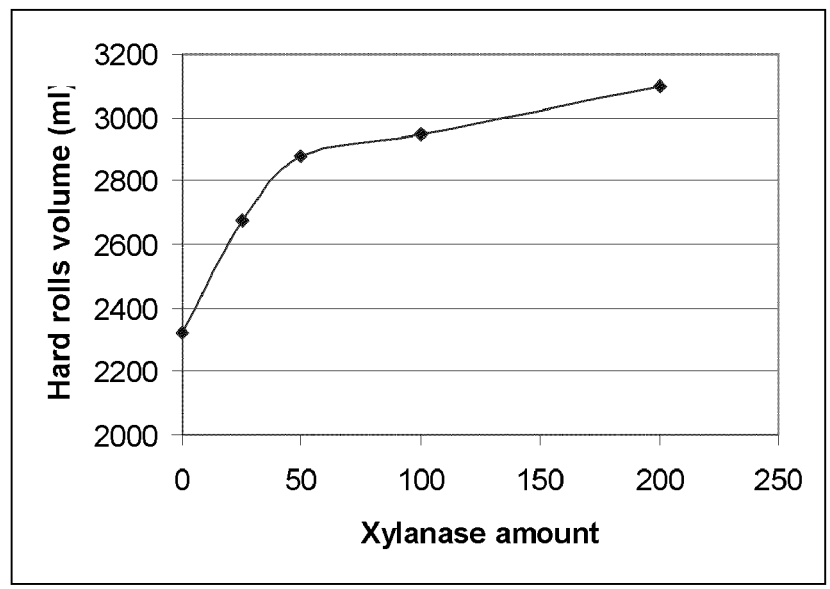
FIG. 1 represents the effect of increasing amounts of *Pseudoalteromonas haloplanktis* xylanase TAH3a on the volume of Belgium hard rolls.

Lane 1: molecular weight markers.

Lanes 2-5: amounts of *Pseudoalteromonas haloplanktis* xylanase (2-3) and *Bacillus subtilis* xylanase (4-5) needed to treat respectively 0.333 (2, 4) and 0.166 kg (3, 5) of wheat flour.

The invention will be described in further details in the following examples and embodiments by reference to the enclosed drawings. Particular embodiments and examples are not in any way intended to limit the scope of the invention as claimed.

DETAILED DESCRIPTION OF THE INVENTION

The present invention in particular relates to the use of family 8 enzymes with xylanolytic activity in baking to improve among others the loaf volume. Said enzymes may have other activities, but the xylanolytic activity should be such that the enzyme is suited for the purposes of the present invention.

A. Preparation of Some Preferred Enzymes According to the Invention

Enzymes with xylanolytic activity from the glycosyl hydrolases family 8 can be obtained from various sources (see e.g. http://afmb.cnrs-mrs.fr/CAZY/ for an overview). Some of the enzymes have been described in the scientific literature and may therefore be obtained using the techniques described in the corresponding publications. Below, the preparation of some preferred enzymes according to the invention is described in more details.

A.1. Xylanase from *Pseudoalteromonas haloplanktis* TAH3a

The xylanase from *Pseudoalteromonas haloplanktis* TAH3a has been described in Collins T. et al. (2002. A novel Family 8 xylanase: functional and physico-chemical characterisation. J. Biol. Chem. Vol. 277(38), p 35133). Collins et al. describes the preparation by liquid culture of a recombinant strain of *Escherichia coli* carrying the *Pseudoalteromonas haloplanktis* TAH3a xylanase gene cloned in an expression plasmid.

The nucleotide sequence of the xylanase gene of *Pseudoalteromonas haloplanktis* is available, as well as is available the corresponding amino acid sequence (EMBL Accession number AJ427921, sequence enclosed by reference thereto, SEQ ID NOS: 6-7). The enzyme has a molecular weight of 46000 Da, an isoelectric point of approximately 9.5, an optimum temperature of 35° C. and an optimum pH between 5.3 and 8. It is a true xylanase with the main reaction products of xylan hydrolysis being xylotriose and xylotetraose after prolonged incubation.

Crude or purified preparation of this xylanase can be obtained by first cultivating either the wild-type of the recombinant strain in a medium suitable to express the enzyme eventually followed by one or several steps of purification such as but not limited to centrifugation, cell disruption, microfiltration, ultrafiltration, precipitation, liquid chromatography, freeze-drying, . . . .

A.2. Xylanase Y from *Bacillus halodurans* C-125

The sequence of the family 8 xylanase Y from *Bacillus halodurans* strain C-125 (ATCCCBAA-125) is available as GenBank/GenPept™ accession code BAB05824 (sequence enclosed by reference thereto, SEQ ID NO: 8). The corresponding DNA sequence is available as part as the complete genome sequence of *Bacillus halodurans* strain C-125 (accession code AP001514, sequence enclosed by reference thereto).

The xylanase from *Bacillus halodurans* C-125 may be obtained by first culturing the strain in/on a medium suitable for expressing the xylanase followed by one or several steps of purification such as but not limited to centrifugation, cell disruption, microfiltration, ultrafiltration, precipitation, liquid chromatography, freeze-drying, . . . .

Alternatively, the xylanase from *Bacillus halodurans* C-125 may be obtained by first cloning the corresponding gene using well known techniques such as PCR amplification, ligation to a vector and transformation in a microbial host. After this step, the xylanase may be advantageously expressed in a suitable host by placing the gene under the control of appropriate control sequences such as but not restricted to promoter and terminator and inserting this DNA construct in a cell that would permit the expression of the gene.

In a specific embodiment of the present invention the xylanase gene will be overexpressed in said cell.

The present invention is, however, not restricted to the above enzymes but extends to other enzymes with xylanolytic activity belonging to the glycosidase hydrolases family 8. These enzymes are produced by microbial and non-microbial living cells such as but not restricted to plants or animals. The enzymes may be obtained directly from living cell cultures and/or samples, or may be produced by recombinant strains or host cells. The gene encoding the enzyme of interest may be a synthetic gene.

By "recombinant strain" or by "recombinant host cell" is meant a strain having incorporated the nucleotide sequence of said enzymes with xylanolytic activity belonging to the glycosidase hydrolases family 8.

Advantageously, recombinant host cells are selected from the group consisting of the microbial world, preferably bacteria or fungi, including yeast and more preferably *Bacillus*.

Preferably, said recombinant strain is capable of overexpressing said nucleotide sequence and allows advantageously a high production of the said xylanase.

The enzymes with xylanolytic activity produced according to the present invention can be used directly for the purpose of the said present invention and/or may undergo one or more purification or (further) culturing steps. In a particular embodiment of the invention, the enzymes may be used in pure form.

Possible preparation methods for enzymes according to the invention include among others preparation or purification from cultures of microorganisms, recombinant or not, in shake flasks or in fermentors, preparation or purification from immobilized cultures, extraction and/or purification from living cells (plants, . . . ), B. Application of the Enzyme The enzyme with xylanolytic activity according to the present invention, purified or not purified, is particularly suited as bread-improving agent. Bread-improving agents are products that could improve or increase texture, flavour, anti-staling effects, softness, crumb softness upon storage, freshness, dough machinability, volume of a final product. Preferably, said enzyme with xylanolytic activity improves the dough handling and/or increases the specific volume of the final baked product. "Baked product" intends to include any product prepared from dough, in particular a yeast raised baked product. Dough is obtained from any type of flour or meal (e.g. based on wheat, rye, barley, oat, or maize). Preferably, dough is prepared with wheat or with mixes including wheat.

It is one of the aspect of the present invention to show that the enzymes with xylanolytic activity belonging to the family 8 could advantageously be used in a bread improver formula.

In a further embodiment of the present invention, it is shown that an enzyme with xylanolytic activity belonging to glycoside hydrolases family 8 increases the loaf volume of a baked product.

In a further embodiment of the present invention, it is shown that the amount of a family 8 enzyme with xylanolytic activity needed to obtain a particular result in baking is exceptionally lower than the amount generally used when working with commercially available enzymes.

In a further aspect, the present invention relates to the additive effect of said enzyme with xylanolytic activity with other enzymes, in particular with an alpha-amylase, preferably an alpha-amylase from *Aspergillus oryzae*. Said enzyme with xylanolytic activity may be used in combination with other bread-improving agents like but not limited to enzymes, emulsifiers, oxidants, milk powder, fats, sugars, amino acids, salts, proteins (gluten, cellulose binding site), such improving agents being well known to persons skilled in the art. Examples of enzymes are but not restricted to alpha-amylases, beta-amylases, maltogenic amylases, xylanases, proteases, glucose oxidase, oxido-reductases, glucanases, cellulases, transglutaminases, isomerases, lipases, phospholipases, pectinases, etc.

The enzyme with xylanolytic activity according to the present invention may be used under several forms. Cells expressing the enzyme, such as yeast, fungi, Archea bacteria or bacteria, may be used directly in the process. Said enzyme may be used as a cell extract, a cell-free extract (i.e. portions of the host cell that has been submitted to one or more disruption, centrifugation and/or extraction steps) or as a purified protein. Any of the above-described forms may be used in combination with another enzyme under any of the above-described forms. Said cells, cell extracts, cell-free extracts or enzymes may be mixed with different ingredients, e.g. in the form of a dry powder or a granulate, in particular a non-dusting granulate, in a form of a liquid, for example with stabilisers such as polyols, sugars, organic acids, sugar alcohols according to established methods.

EXAMPLES

Example 1

Preparation of the Xylanase of *Pseudoalteromonas haloplanktis* TAH3a

The xylanase from *Pseudoalteromonas haloplanktis* was obtained as described (Collins et al, 2002, see above) from a liquid culture of a recombinant strain of *Escherichia coli* transformed with a DNA vector containing the corresponding gene.

Example 2

Preparation of the Xylanase from *Bacillus halodurans* C-125

Bacterial Strain and Culture Conditions

*Bacillus halodurans* C-125 (ATCC BAA-125) was cultivated in Alkaline *Bacillus* medium (10 g/l glucose, 5 g/l yeast extract (Difco), 10 g/l Bacto Tryptone (Difco), 1 g/l $K_2HPO_4$, 0.2 g/l $MgSO_4$, 10 g/l $Na_2CO_3$) supplemented with 10 g/l birchwood xylan (Sigma) for 72 hours at 37° C. After centrifugation for 1 h at 18000 g and 4° C. the supernatant was concentrated by precipitation with 80% ammonium sulphate and resuspended in 20 mM MOPS at pH 8.0. This fraction represents the crude extract fraction that will be used for the baking trials.

Cloning and Overexpression of the Xylanase Y Gene

Genomic DNA was extracted and purified from 16 hour cultures, cultivated at 37° C. in the modified Alkaline *Bacillus* medium described above, with the Wizard® Genomic DNA Purification kit (Promega). Based on the published sequence (GenBank/GenPept™ accession AP001514) the entire xylanase Y gene was PCR-amplified using VENT polymerase (Biolabs Inc, Beverly, Mass., USA) with the sense primer 5'-GGGCATATGAAGAAAACGACAGAAGG TG-3', SEQ ID NO: 1 containing an Nde I site (underlined) and with the antisense primer 5'-GGCTCGAGCTAG TGTTCCTCT-TCTTG-3', SEQ ID NO: 2 containing an Xho I site (underlined) and the stop codon (in italics).

After 3 min initial denaturation at 95° C., 25 cycles of amplification were performed using a Progene apparatus (Techne Cambridge, UK). Each cycle included denaturation at 95° C. for 1 min, hybridization at 52° C. for 30 sec, and elongation at 72° C. for 1.5 min.

The PCR product was cloned into a PCRScript Amp SK(+) vector (Stratagene), using the procedure recommended by the supplier, and used to transform Epicurian Coli XL10-Gold® Kan ultracompetent cells. Blue-white selection allowed selection of white colonies carrying the PCR-fragment. Purified plasmid preparation (Nucleospin plasmid, Macherey-Nagel) was sequenced on an ALF DNA sequencer (Pharmacia Biotech). Sequencing of the inserted fragment was carried out using the universal primers T7 and RP as well as the following primers:

```
5'-GTGCGGACTGAAGGAATGTC-3',      SEQ ID NO: 3

5'-GTATGGTCCATCAACAGAGG-3',      SEQ ID NO: 4

5'-GATGGCACTAAAAACTCCTGG-3'.     SEQ ID NO: 5
```

The sequence obtained was identical to the published sequence that could be retrieved from GenBank/genPept™ with the accession number AP001514.

The xylanase Y gene hence cloned in the PCRScript Amp SK(+) was then excised with Nde I and Xho I and ligated into the pET 22b(+) cloning vector (Novagen). The resulting recombinant plasmid was transformed to *E. coli* BL21 (DE3) cells (Stratagene).

Production of the Recombinant Family 8 Xylanase Y from *Bacillus halodurans* C-125.

Fifteen ml of a five hour preculture (37° C.) of the *E. coli* BL21 (DE3) cells carrying the xylanase gene was centrifuged at 10000 g for 1 minute and the pellet was resuspended in 900 ml Terrific broth (12 g/l Bacto tryptone (Difco), 24 g/l yeast extract (Difco), 4 ml/l glycerol, 12.54 g/l $K_2HPO_4$, 2.31 g/l $KH_2PO_4$) containing 200 µg/ml ampicillin in a 3 liter shake flask. The culture was incubated at 37° C. and 250 rpm until an absorbance at 550 nm of between 3-4 was reached whereupon the expression of the enzyme was induced with 1 mM isopropyl-1-thio-β-galactopyranoside. Following 15 hours further incubation at 37° C. the cells were harvested by centrifugation at 18000 g for 30 minutes at 4° C., resuspended in 50 mM BICINE containing 10 mM NaCl, disrupted in a prechilled cell disrupter (Constant Systems Ltd., Warwick, UK) at 28 Kpsi and centrifuged at 40,000 g for 30 minutes. Production of the Recombinant *Bacillus halodurans* C-125 Family 8 Xylanase.

The cells of a five hour preculture (37° C.) of the *E. coli* BL21(DE3) cells carrying the xylanase gene were collected by centrifugation at 10,000 g for 1 minute and used to inoculate five liters (15 ml preculture per liter of culture) of Terrific broth (12 g/l Bacto tryptone (Difco), 24 g/l yeast extract (Difco), 4 ml/l glycerol, 12.54 g/l $K_2HPO_4$, 2.31 g/l $KH_2PO_4$) containing 200 μg/ml ampicillin. The culture was incubated at 37° C. and 250 rpm until an absorbance at 550 nm of between 3-4 was reached whereupon the expression of the enzyme was induced with 1 mM isopropyl-1-thio-β-galactopyranoside. Following 4 hours further incubation at 37° C. the cells were harvested by centrifugation at 18000 g for 20 minutes at 4° C., resuspended in 20 mM MOPS (Sigma), disrupted in a prechilled cell disrupter (Constant Systems Ltd.) at 28 Kpsi and centrifuged at 40,000 g for 30 minutes. Chromosomal DNA was removed by treatment with 0.2% protamine sulfate (Calbiochem) and centrifugation at 40,000 g for 30 minutes. 25 units of benzonase (Merck, Darmstadt, Germany) was then added and the solution used in baking trials.

Example 3

Effect of the Xylanase of *Pseudoalteromonas haloplanktis* TAH3a in Baking of Belgian Hard Rolls Baking trials were performed to demonstrate the positive effect of *Pseudoalteromonas haloplanktis* TAH3a xylanase in baking. The positive effect was evaluated by the increase in bread volume compared to a reference not containing this enzyme.

The xylanase was tested in Belgian hard rolls that are produced on a large scale every day in Belgium. The procedure described is well known to the craft baker and it is obvious to one skilled in the art that the same results may be obtained by using equipment from other suppliers.

The ingredients used are listed in the table 1 below:

TABLE 1

| Ingredients (g) | RECIPE 1 | RECIPE 2 | RECIPE 3 | RECIPE 4 | RECIPE 5 |
| --- | --- | --- | --- | --- | --- |
| Flour (Surbi-Molens van Deinze) | 1500 | 1500 | 1500 | 1500 | 1500 |
| Water | 915 | 915 | 915 | 915 | 915 |
| Fresh yeast (Bruggeman-Belgium) | 90 | 90 | 90 | 90 | 90 |
| Sodium chloride | 30 | 30 | 30 | 30 | 30 |
| Multec Data HP 20 (Beldem-Belgium) | 3.9 | 3.9 | 3.9 | 3.9 | 3.9 |
| Ascorbic acid | 0.12 | 0.12 | 0.12 | 0.12 | 0.12 |
| Xylanase Pseudoalter. Haloplanktis (units (1)/100 kg flour) | 0 | 25 | 50 | 100 | 200 |

(1) One unit of *Pseudoalteromonas haloplanktis* xylanase is defined as the amount of enzyme needed to release 1 μmole of reducing sugar (expressed as xylose) from birchwood xylan at 30° C. and pH 4.5 (Nelson-Somogyi method)

The ingredients were mixed for 2 min at low and 8 min at high speed in a Diosna SP24 mixer. The final dough temperature as well as the resting and proofing temperatures were 25° C. After resting for 15 min at 25° C., the dough was reworked manually and rested for another 10 min. Afterwards, 2 kg dough pieces were made up and proofed for 10 min. The 2-kg dough pieces were divided and made up using the Eberhardt Optimat. 66 gr. round dough pieces were obtained. After another 5 min resting time, the dough pieces were cut by pressing and submitted to a final proofing stage for 70 min. The dough pieces were baked at 230° C. in a MIWE Condo™ oven with steam (Michael Wenz-Arnstein-Germany). The volume of 6 rolls was measured using the commonly used rapeseed displacement method.

The results are presented on the table 2 below:

TABLE 2

| Xylanase units | Rolls volume (ml) |
| --- | --- |
| 0 | 2325 |
| 25 | 2675 |
| 50 | 2875 |
| 100 | 2950 |
| 200 | 3100 |

A graphical representation of the effect of the xylanase is shown on FIG. 1.

These results show that the xylanase of *Pseudoalteromonas haloplanktis* has a positive effect on the volume of bread.

Example 4

Comparison of Xylanase Amounts Used in Baking

The relative amount of xylanases needed to obtain the same effect on the volume in the Belgian hard rolls assay described in Example 3 has been compared by SDS-polyacrylamide gel electrophoresis.

The xylanases tested and their respective usage levels in baking were the following:
the xylanase from *Pseudoalteromonas haloplanktis* TAH3a (30 *P. Haloplanktis* units/100 kg flour)
the xylanase from *Bacillus subtilis* (Belase B210 (BELDEM S.A., Belgium)—3 g/100 kg flour).

Amounts of enzyme corresponding to the quantity needed to treat 0.333 kg and 0.166 kg of flour, and resulting in the same volume increase, were loaded on a 12% Tris-HCl precast gel for SDS-polyacrylamide electrophoresis "Ready Gel" (BIO-RAD, Hercules, Calif., USA) and run in a "Mini Protean II" (BIO-RAD) apparatus according to the procedure of the manufacturer. Proteins were stained with Coomassie blue using standard procedure.

Figure 2:
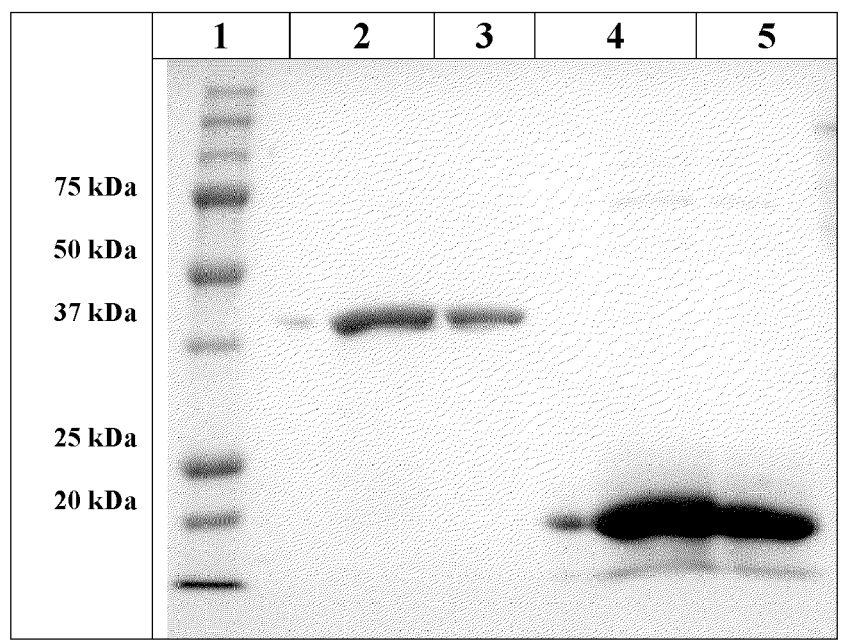
FIG. 2 shows a SDS-polyacrylamide gel electrophoresis of various xylanase samples (amount of enzyme loaded proportional to the amount used in baking, same proportionality factor for all enzymes).

A picture of the stained gel is shown on FIG. 2.

It can be concluded from this picture that the amount of xylanase from *Pseudoalteromonas haloplanktis* TAH3a needed in baking is significantly lower compared to the other.

Example 5

Effect of the Xylanase of *Pseudoalteromonas haloplanktis* TAH3a in Argentinian Breads Baking trials were performed to demonstrate the positive effect of a family 8 xylanases in baking in another recipe than the one used for example 3, such as for instance in Argentinian breads. The positive effect was evaluated by the increase in bread volume compared to a reference not containing the enzyme and by the width of the cut on the surface of the bread.

The enzymes of the invention were tested in Argentinian breads that are typical long bread which need long time proofing (17 hours at 20° C.). The procedure described is well known to the craft baker and it is obvious to one skilled in the art that the same results may be obtained by using equipment from other suppliers.

The ingredients used are listed in the table 3 below:

TABLE 3

| Ingredients (g) | RECIPE 1 | RECIPE 2 | RECIPE 3 | RECIPE 4 |
|---|---|---|---|---|
| Flour (Surbi-Molens van Deinze-Belgium) | 1500 | 1500 | 1500 | 1500 |
| Water | 810 | 810 | 810 | 810 |
| Fresh yeast (Bruggeman-Belgium) | 5.25 | 5.25 | 5.25 | 5.25 |
| Sodium chloride | 30 | 30 | 30 | 30 |
| Standard Improver(1) (Puratos-Belgium) | 22.5 | 22.5 | 22.5 | 22.5 |
| Bel'ase B210 (Beldem-Belgium) (210 units/g) | 0 | 0.15 | 0 | 0 |
| Purified Xylanase of *Pseudoalteromonas. haloplanktis* TAH3a (units(2)/100 kg flour) | 0 | 0 | 25 | 50 |

(1)The standard improver used contains: Fungal alpha amylase (Fungamyl 75.000, Novozymes) 1 g/100 kg flour, vitamin C 10 g, Azodicarbonamide 2 g/100 kg flour. This is an example of a standard improver. Absolute and relative amounts of additives can vary according to local adaptation to wheat flour and process
(2)One unit of xylanase is defined as the amount of enzyme needed to release 1 μmole of reducing sugar (expressed as xylose) from birchwood xylan at 30° C. and pH 4.5 (Nelson-Somogyi method)

The ingredients were mixed for 2 min at low and 7 min at high speed in a Diosna SP24 mixer. The final dough temperature during the resting was 25° C. while it was 20° C. during proofing. After resting for 20 min at 25° C., the dough was reworked manually and rested for 17 hours at 20° C. during proofing. Afterwards, 2 kg dough pieces were made up and proofed for 10 min. The 0.35-kg dough pieces were divided and made up using the Bertrand R8/L8 (+/−30 cm) and submitted to a final proofing stage for 17 hours. The dough pieces were baked at 210° C. for 30 min in a MIWE Condo™ oven with steam (Michael Wenz-Arnstein-Germany). The volume of Argentinian breads was measured using the commonly used rapeseed displacement method.

The results are presented on the table 4 below:

TABLE 4

| Recipe | Sample | Xylanase units | Bread volume (ml) | Width of cut (mm) |
|---|---|---|---|---|
| 1 | | 0 | 1675 | 19 |
| 2 | Bel'ase B210 | 2100 | 1900 | 27 |
| 3 | TAH3a | 25 | 1900 | 34 |
| 4 | TAH3a | 50 | 1925 | 30 |

These results show that the family 8 xylanase has a positive effect on bread making with long time proofing at lower temperature (i.e. 20° C.). The amount of the commercial enzyme (Bel'ase B210, see above) used here is 3-fold higher than the optimal dose required as described in example 3 for Belgian hard rolls, while the amount of family 8 xylanase needed remained unchanged. There exists also a difference between the enzyme concentration needed to optimize the width of the cut and the one needed for an optimal volume increase.

Example 6

The Effect of Various Enzymes of the Invention Versus Other Enzymes in Baking Baking trials were performed to demonstrate the positive effect of various enzymes with xylanolytic activity belonging to the glycoside hydrolases family 8 in baking. The positive effect was evaluated by the increase in bread volume compared to a reference not containing these enzymes as well as to a commercial enzyme preparation (Bel'ase B210, see above).

The xylanase from *Pseudoalteromonas haloplanktis* TAH3a was prepared and purified as described in example 1. The xylanase Y from *Bacillus halodurans* C-125 was prepared from a recombinant *Escherichia coli* strain as described in example 2.

The method used to evaluate the performances of the two enzymes was a mini baking test consisting of preparing dough with 100 g of flour.

The procedure described is well known to one skilled in the art and it is obvious that the same results may be obtained by using equipment from other suppliers.

The ingredients used are listed in the table 5 below:

TABLE 5

| Ingredients (g) | RECIPE 1 | RECIPE 2 | RECIPE 3 | RECIPE 4 | RECIPE 5 | RECIPE 6 | RECIPE 7 |
|---|---|---|---|---|---|---|---|
| Flour (Surbi-Molens van Deinze) | 100 | 100 | 100 | 100 | 100 | 100 | 100 |
| Water | 57 | 57 | 57 | 57 | 57 | 57 | 57 |
| Fresh yeast (Bruggeman-Belgium) | 5 | 5 | 5 | 5 | 5 | 5 | 5 |
| Sodium chloride | 2 | 2 | 2 | 2 | 2 | 2 | 2 |
| Dextrose | 2 | 2 | 2 | 2 | 2 | 2 | 2 |

TABLE 5-continued

| Ingredients (g) | RECIPE 1 | RECIPE 2 | RECIPE 3 | RECIPE 4 | RECIPE 5 | RECIPE 6 | RECIPE 7 |
|---|---|---|---|---|---|---|---|
| Ascorbic acid (g/100 kg flour) | 4 | 4 | 4 | 4 | 4 | 4 | 4 |
| Bel'ase B210 (Beldem-Belgium) (units (1)/100 kg flour) | 0 | 630 | 1050 | 0 | 0 | 0 | 0 |
| Purified xylanase from *Pseudoalteromonas haloplanktis* TAH3a (units (1)/100 kg flour) | 0 | 0 | 0 | 25 | 50 | 0 | 0 |
| Recombinant xylanase from *Bacillus halodurans* C-125 (units (1)/100 kg flour) | 0 | 0 | 0 | 0 | 0 | 6000 | 12000 |

(1) One unit of xylanase is defined as the amount of enzyme needed to release 1 μmole of reducing sugar (expressed as xylose) from birchwood xylan at 30° C. and pH 4.5 (Nelson-Somogyi method)

The ingredients were mixed for 4.5 min in a National mixer. 150 g dough pieces were weighted and rested for 20 min at 25° C. in plastic boxes. The doughs were reworked and rested for another 20 min. The final proofing time was 50 min at 36° C. The dough pieces were then baked at 225° C. for 20 min. The volume of the breads was measured using the commonly used rapeseed displacement method.

The results are presented on the table 6 below:

TABLE 6

| Recipe | Sample | Xylanase units/ 100 kg flour | Bread volume (ml) |
|---|---|---|---|
| 1 |  | 0 | 650 |
| 2 | Bel'ase B210 | 630 | 680 |
| 3 | Bel'ase B210 | 1050 | 705 |

TABLE 6-continued

| Recipe | Sample | Xylanase units/ 100 kg flour | Bread volume (ml) |
|---|---|---|---|
| 4 | TAH3a | 25 | 690 |
| 5 | TAH3a | 50 | 760 |
| 6 | C-125 | 6000 | 725 |
| 7 | C-125 | 12000 | 725 |

These results show that the positive effect of enzymes of the invention is not restricted to the *Pseudoalteromonas haloplanktis* TAH3a xylanase. Also other enzyme preparations with xylanolytic activity belonging to the glycoside hydrolase family 8 could improve the properties of bread (demonstrated here for the *Bacillus halodurans* C-125 xylanase, other results not shown).

What is claimed is:

1. An isolated psychrophilic Family 8 glycoside hydrolase enzyme with xylanolytic activity which is obtained from *Pseudoalteromonas haloplanktis*, and which comprises the amino acid sequence of SEQ ID NO 7.

2. The isolated enzyme of claim 1, which has a molecular weight of about 46000 Da, an isoelectric point of approximately 9.5, an optimum temperature of about 35° C. and an optimum pH between about 5.3 and 8.

3. The isolated enzyme of claim 1, which hydrolyses the substrate with inversion of configuration.

4. The isolated enzyme of claim 1, which is obtained from *Pseudoalteromonas haloplanktis* TAH3a.

5. A composition comprising the enzyme of claim 1.

6. A composition comprising the enzyme of claim 2.

* * * * *